United States Patent
Nagase et al.

(10) Patent No.: US 8,333,737 B2
(45) Date of Patent: Dec. 18, 2012

(54) SYSTEMS AND METHODS FOR A MEDICAL SYRINGE

(75) Inventors: Shinya Nagase, Hayward, CA (US); Shenna Tang, Dalian (CN); Penghai Zhao, Dalian (CN)

(73) Assignee: JMS North America Corporation, Hayward, CA (US)

( * ) Notice: Subject to any disclaimer, the term of this patent is extended or adjusted under 35 U.S.C. 154(b) by 308 days.

(21) Appl. No.: 12/793,380

(22) Filed: Jun. 3, 2010

(65) Prior Publication Data

US 2011/0301547 A1  Dec. 8, 2011

(51) Int. Cl.
*A61M 5/32* (2006.01)

(52) U.S. Cl. ........................................................ 604/192

(58) Field of Classification Search .................. 604/110, 604/111, 187, 188, 192, 198, 167.06, 168.01
See application file for complete search history.

(56) References Cited

U.S. PATENT DOCUMENTS

| | | | |
|---|---|---|---|
| 4,252,118 A | 2/1981 | Richard et al. | |
| 4,573,977 A | 3/1986 | Crawford | |
| 4,743,233 A | 5/1988 | Schneider | |
| 5,746,733 A | 5/1998 | Capaccio et al. | |
| 5,776,125 A | 7/1998 | Dudar et al. | |
| 5,782,803 A | 7/1998 | Jentzen | |
| 5,814,017 A | 9/1998 | Kashmer | |
| 5,902,269 A | 5/1999 | Jentzen | |
| 5,902,270 A | 5/1999 | Jentzen | |
| 5,902,271 A | 5/1999 | Jentzen | |
| 5,902,277 A | 5/1999 | Jentzen | |
| 5,964,737 A | 10/1999 | Caizza | |
| 6,331,174 B1 | 12/2001 | Reinhard et al. | |
| 6,368,303 B1 | 4/2002 | Caizza | |
| 6,517,516 B1 | 2/2003 | Caizza | |
| 6,565,551 B1 | 5/2003 | Jones et al. | |
| 6,632,198 B2 | 10/2003 | Caizza | |
| 6,673,044 B2 * | 1/2004 | Righi et al. | 604/110 |
| 6,699,222 B1 | 3/2004 | Jones et al. | |
| 6,840,291 B2 | 1/2005 | Caizza et al. | |
| 2006/0200085 A1 | 9/2006 | Watts et al. | |
| 2007/0060904 A1 | 3/2007 | Vedrine et al. | |
| 2008/0033347 A1 | 2/2008 | D'Arrigo et al. | |
| 2008/0033370 A1 | 2/2008 | D'Arrigo et al. | |
| 2008/0058731 A1 * | 3/2008 | Wu | 604/218 |
| 2008/0195054 A1 | 8/2008 | Snarp et al. | |

OTHER PUBLICATIONS

PCT/US2011/039124 filed Jun. 3, 2011 International Search Report dated Sep. 27, 2011.
PCT/US2011/039124 filed Jun. 3, 2011 Written Opinion dated Sep. 27, 2011.

* cited by examiner

*Primary Examiner* — Christopher D Koharski
(74) *Attorney, Agent, or Firm* — Rutan & Tucker, LLP

(57) ABSTRACT

Systems and methods for administering drugs to a patient, including a syringe system. The syringe system includes a plastic needle coupled to an end of a syringe barrel, the needle including a proximal taper and a distal taper. A cannula assembly is removably coupled to the plastic needle, the cannula including mating surfaces for the proximal and distal tapers of the plastic needle. The syringe system can also include a cannula cover with a first and second end with different sizes to respectively attach to the cannula assembly and the barrel when the cannula assembly is removed. The cannula may have a distal tip cut at an angle to ensure maximum removal of drug from a given vial.

18 Claims, 5 Drawing Sheets

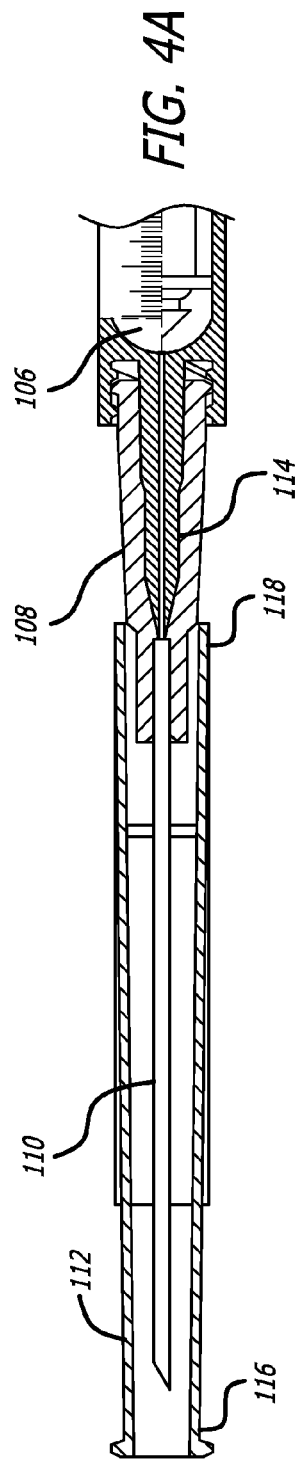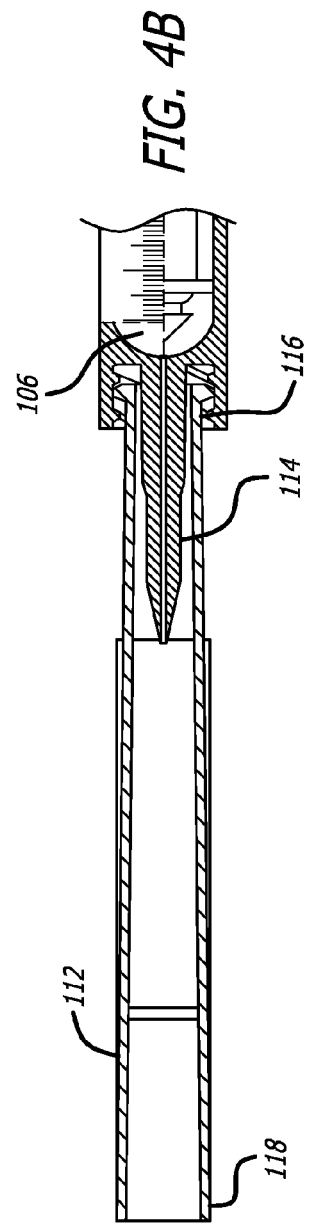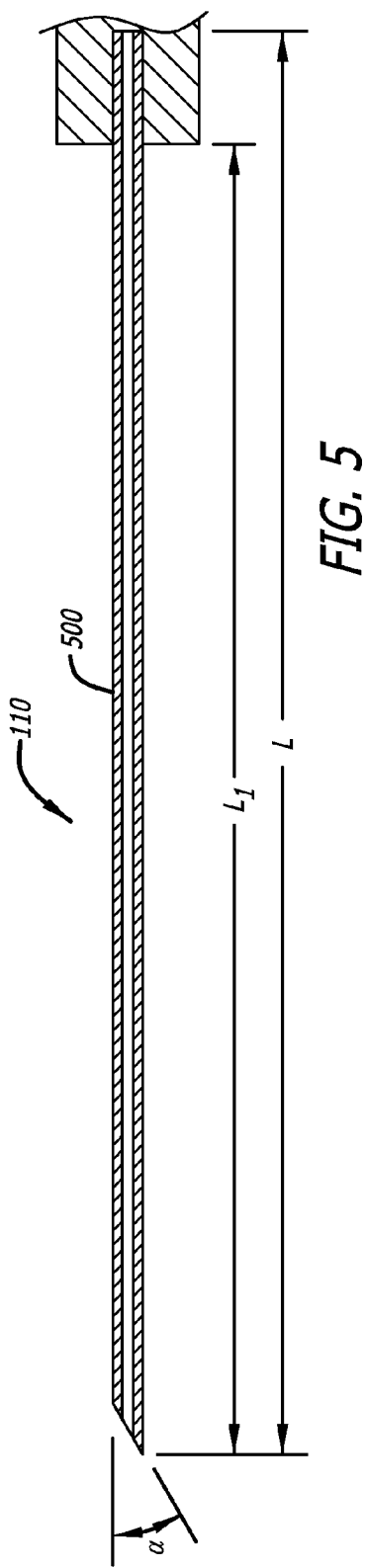

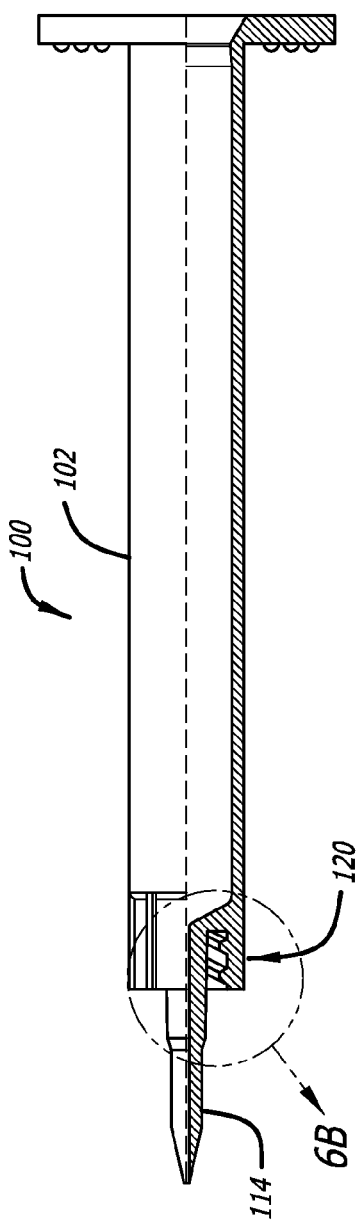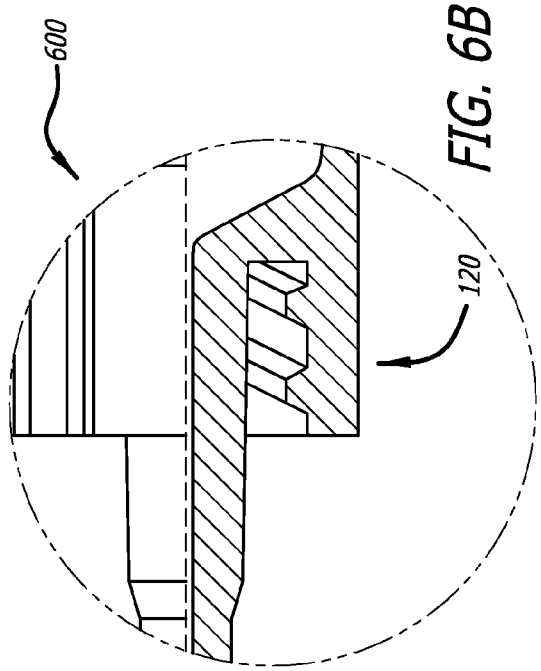

SYSTEMS AND METHODS FOR A MEDICAL SYRINGE

FIELD

This invention generally relates to systems and methods for medical devices and more particularly, some embodiments relate to medical syringe systems and methods related to such syringes.

BACKGROUND

In many cases, hypodermic syringes are used to deliver medication to patients. These syringes typically include various "dead-spaces" within the syringe between various components of the syringe. A dead-space is an area that may contain a substance that is not generally delivered to a patient during an injection. For example, a typical syringe can trap medication between the end of the plunger and the wall of the syringe or within an end portion of the syringe that holds the needle, but is smaller in diameter than the plunger.

Small quantities of drugs can be wasted because of these dead-spaces. Due to the great expense of certain drugs, even a small amount of wasted material per vial or container is magnified when viewed in terms of the total number of vials or containers sold. Also, because the use of syringes is very common, small amounts of wasted drugs can add up to a large amount when aggregated together. Additionally, trapping higher quantities of these drugs may make it more likely that the drugs get into the environment if they are later able to escape from the discarded syringes. Accordingly, it can be beneficial to design, manufacture, and use syringes that reduce dead-spaces.

Further, in many cases it can be expensive to dispose of used syringes. If a single piece syringe is used to administer a drug to a patient, the volume of waste that includes needles can be high. Additionally, after coming into contact with a patient or a patient's bodily fluids the waste must be disposed of as biological waste. Syringes that include a separable needle portion and syringe body portion, however, may still be expensive to dispose of because, while the volume of waste that includes needles may be lower, both portions are biological waste after the needle and the syringe come into contact with a patient or a patient's bodily fluids.

Additionally, needles can be dangerous to handle and work with. Needle sticks can be common and may lead to the spread of disease from, for example, a patient to a medical worker. Accordingly, it may be beneficial to use medical delivery systems that eliminate or limit the number of needles used to provide a drug or other substance to a patient intravenously, or by other methods that involve piercing the skin, e.g., injection directly into the muscle.

SUMMARY

In one embodiment, a syringe system, including a barrel, plunger and piston, includes a plastic needle coupled to an end of the barrel, the needle including a proximal taper at a proximal end of the needle, tapering from a proximal first end to a proximal second end toward a longitudinal axis of the needle from a first diameter of the needle to a second diameter of the needle less than the first diameter, the needle further including a distal taper at a distal tip of the needle, tapering from a distal first end to a distal second end toward the longitudinal axis from the second diameter to a third diameter of the needle less than the second diameter, the distal first end separated from the proximal second end, and a cannula assembly including a cannula and cannula hub, the cannula hub having an internal first mating surface that contacts the proximal taper of the needle and an internal second mating surface that contacts the distal taper of the needle, the cannula assembly removably coupled to the plastic needle.

In another embodiment, a syringe system, including a barrel, plunger and piston, includes a plastic needle coupled to an end of the barrel, the needle including a proximal taper at a proximal end of the needle, tapering from a proximal first end to a proximal second end toward a longitudinal axis of the needle from a first diameter of the needle to a second diameter of the needle less than the first diameter, the needle further including a distal taper at a distal tip of the needle, tapering from a distal first end to a distal second end toward the longitudinal axis from the second diameter to a third diameter of the needle less than the second diameter, a cannula assembly removably coupled to the plastic needle, and a cannula cover having a first end, including a first internal surface mating with an exterior surface of the cannula assembly for removable attachment thereto, and a second end opposite the first send, including a second internal surface mating with an exterior surface of the barrel for removable attachment thereto.

In yet another embodiment, a syringe system, including a barrel, plunger and piston, includes a plastic needle coupled to an end of the barrel, the needle including a proximal taper at a proximal end of the needle, tapering from a proximal first end to a proximal second end toward a longitudinal axis of the needle from a first diameter of the needle to a second diameter of the needle less than the first diameter, the needle further including a distal taper at a distal tip of the needle, tapering from a distal first end to a distal second end toward the longitudinal axis from the second diameter to a third diameter of the needle less than the second diameter, the distal first end separated from the proximal second end, and a cannula assembly removably coupled to the plastic needle, including a cannula having a distal tip cut at an angle $\alpha$ to match a portion of an interior surface of a drug vial, wherein the cannula is positioned in alignment with the portion of the interior surface of the vial to remove substantially all of a material from the drug vial, and a cannula hub having an internal first mating surface that contacts the proximal taper of the needle and an internal second mating surface that contacts the distal taper of the needle.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 4A-4B are diagrams illustrating an example cannula cover in accordance with an embodiment of the systems and methods described herein;

FIG. 5 is a diagram illustrating a cannula in accordance with an embodiment of the systems and methods described herein;

FIGS. 6A-6B are diagrams illustrating a plastic needle and barrel in accordance with an embodiment of the systems and methods described herein;

DETAILED DESCRIPTION

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity, it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Figure 1:
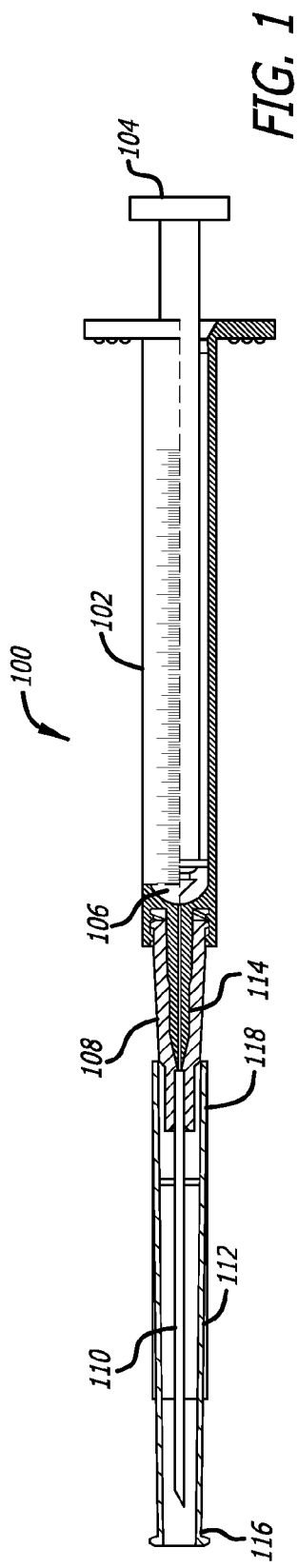
FIG. 1 is a diagram illustrating an example syringe according to one embodiment of the systems and methods described herein.

FIG. 1 is a diagram illustrating an example syringe system 100 according to one embodiment of the systems and methods described herein. Syringe system 100 may, include a barrel 102, a plunger 104, and a piston 106. Plunger 104 may be used to move piston 106 within barrel 102. In this way, fluids, such as medications, can be drawn into the interior of barrel 102 or pushed out of barrel 102.

In the illustrated embodiment of FIG. 1, a cannula hub 108 connects to barrel 102 and is attached to a cannula 110. In various embodiments, cannula 110 can be used to withdrawing medication from a vial. Cannula 110 might not, however, be used to deliver the medication to a patient. A plastic needle 114 might be used to deliver medication to the patient through a preexisting intravenous line. For example, cannula 110 might be sharp enough to pierce the top piece on a vial, while generally not being as sharp as a needle intended to pierce the skin. In most embodiments, the cannula 110 will not be sharp enough to pierce the skin. This may decrease dangers associated with needle sticks from contaminated needles. Additionally, in some embodiments, cannula 110 may be designed to be have a non-coring tip. This can allow for use with medication vials without leaving holes in the tops of the vials that may allow medication to leak or lead to contamination of the medication.

Patients, medical staff, and others may be further protected from the sharp end of cannula 110 by a cannula cover 112. In the illustrated embodiment, cannula cover 112 attaches to cannula hub 108 at first end 118 and extends from it to cover cannula 110. The cover 112 extends beyond the end of cannula 110 to a second end 116 such that contact with the angled end of cannula 110 is generally blocked. Both ends of cannula cover 112 may be open, however, but the ends may generally be small, such that it might be difficult or impossible for a person's skin to be pierced by cannula 110. (If it is even possible for an uncovered cannula 110 to pierce a person's skin.) Cannula cover 112 may friction fit onto cannula hub 108. In other embodiments it may snap fit, screw on, or otherwise be attached to the hub.

Syringe system 100 includes plastic needle 114 with a blunt tip, which is not as sharp as a standard metal needle or cannula 110. Accordingly, when used in the context of a hospital or patient setting, the plastic needle 114 presents less of a risk for accidental needle stick. Plastic needle 114 can be used to introduce medication into a patient by connecting it to a preexisting intravenous line. In this way, the plastic needle 114 does not come into direct contact with the patient because it might only physically contact the intravenous line. Additionally, because the plastic needle 114 has a blunt tip it will not pierce the skin if accidentally coming into contact therewith. Accordingly, if the plastic needle does make contact with a person after use it will be less likely to infect that person. This can lower the probability of the spread of disease from, for example, a patient to a medical worker.

Figure 2:
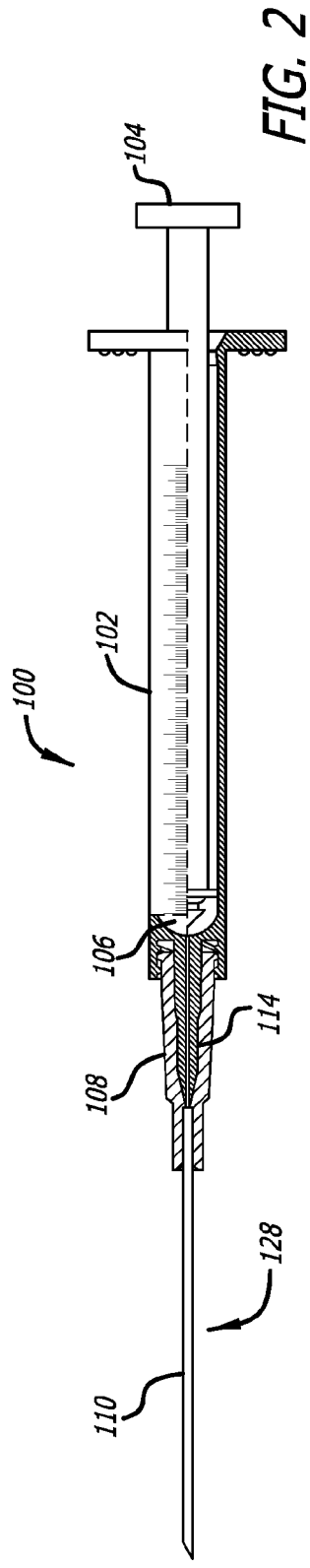
FIG. 2 is a diagram further illustrating the example syringe of FIG. 1.

FIG. 2 is a diagram further illustrating the example syringe of FIG. 1. As illustrated in FIG. 2, cannula cover 112 is removable from the rest of syringe system 100. This allows access to cannula 110 such that cannula 110 can be used to access a vial of medication to withdraw the medication into the interior of barrel 102 of syringe system 100. As illustrated, cannula 110 can be attached to cannula hub 108 to form a cannula assembly 128. Additionally, cannula assembly 128 may be removed from barrel 102 by disconnecting a connection between cannula assembly 128 and barrel 102 at a proximal end of hub 108. Further, cannula hub 108 may have an internal first mating surface that contacts the proximal taper of plastic needle 114. Cannula hub 108 may also have an internal second mating surface that contacts the distal taper of plastic needle 114. Additionally, cannula assembly 128 may be removably coupled to plastic needle 114.

Figure 3:
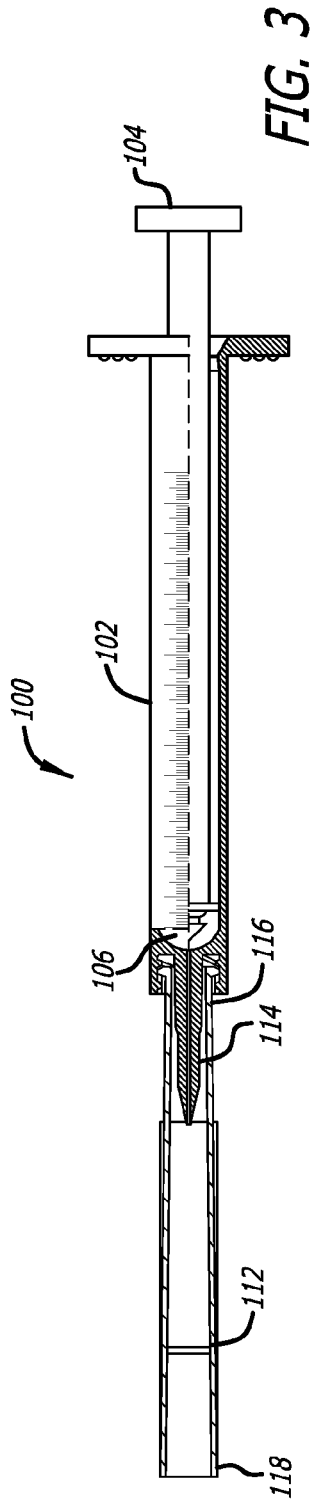
FIG. 3 is a diagram further illustrating the example syringe of FIGS. 1 and 2.

FIG. 3 is a diagram further illustrating the example syringe of FIGS. 1 and 2. FIG. 3 does not include cannula assembly 128, which has been removed from barrel 102. Removal of cannula assembly 128 allows plastic needle 114 to be used to, for example, inject medication into an intravenous line. Cannula cover 112 may be reinstalled on syringe system 100 to cover plastic needle 114 by reversing cannula cover 112 and attaching second end 116 to barrel 102. In this way cannula cover 112 may prevent or lessen contact with plastic needle 114, lowering the probability of contamination of plastic needle 114 and of a needle stick from plastic needle 114. (If such a needle stick is even possible from the general blunt plastic needle 114.)

Accordingly, as illustrated in FIGS. 1 and 3 cannula cover 112 includes a first end with an internal surface shaped to removably attach to an exterior surface of cannula assembly 128. A second end may be shaped to fit over plastic needle 114 when the cannula assembly 128 is removed from plastic needle 114. The second end may be removably attached to a distal end of barrel 102. In some embodiments, various connections between various sub-components may be used. For example, sub-components may be screwed together, snapped together, press fit, welded, interference fit, or bonded using adhesive, solvent, etc.

Additionally, in some embodiments, a modular system, as illustrated in FIGS. 1-3 may decrease or eliminate dead space.

For example, a modular system may be designed to provide medicine to a patient through a pre-existing line, rather than using a needle to pierce the patient's skin. Such a system may decrease dead space because plastic needle 114 may be shorter and have lower volume than a needle or cannula on other syringe systems.

Additionally, in some examples the inside volume of cannula 110 may be reduced, thereby decreasing dead space in cannula 110. For example, the length of cannula 110 might be shorter than a needle that might have to both remove a substance from a vial and inject the substance into a patient. Additionally, the length of such a cannula 110 might be decreased such that it is just long enough to reach the bottom of a vial of medicine, perhaps at an angle to reach the rounded side of the vial. This may also reduce volume of cannula 110 and thereby decrease dead space. In some embodiments, the cannula length can be selected to provide a minimal external clearance. This may minimize bending forces acting on the needle because a decrease in length might decrease the torque applied to the needle for a given force. Additionally, in some systems, needles intended for injection into a patient may be thinner and flimsier. A thicker cannula 110 might also be stronger and might have a smaller internal diameter. The smaller internal diameter may also decrease the internal volume.

Some embodiments may be less prone to pierce a medical practitioner or other person after use. This can decrease dangers associated with needle sticks from contaminated needles. For example, cannula 110 may be designed such that it is not sharp enough to pierce skin, but may pierce a top of a medical vial. Additionally, plastic needle 114 can also be safer for similar reasons.

As illustrated in FIGS. 1 and 3, in some embodiments, the syringe system 100 may include a reversible cannula cover 112 and a removable cannula assembly 128. When the cannula assembly 128 is removed, cannula cover 112 can be reversed and installed on the barrel to protect plastic needle 114 located on the barrel. The cannula can remove a drug from a vial and, after removal of cannula assembly 128, plastic needle 114 can introduce the drug into the patient using a preexisting intravenous line. Plastic needle 114 may include a double taper to provide a seal with a cannula hub that attaches the cannula to the system.

In some embodiments, plastic needle 114 and barrel 102 may be injection molded as a single piece. Other designs might include a separate plastic needle 114 and barrel 102 that may be screwed together, snapped together, bonded, welded, interference fit, etc.

FIGS. 4A-4B are diagrams illustrating an example cannula cover 112 in accordance with an embodiment of the systems and methods described herein. In the illustrated embodiment, cannula cover 112 may be used to cover cannula 110. Additionally, cannula cover 110 may be reversed to attach and cover plastic needle 114 as illustrated in FIG. 4B.

In one embodiment, second end 116 extends beyond the end of cannula 110 to provide some protection from inadvertent sticks, which may also be lessened due to the generally lower sharpness of cannula 110. Some protection against contamination might also be provided. In syringe system 100 cannula cover 112 may provide these protections by attaching cannula cover 112 to cannula hub 108 at first end 118. For example, first end 118 might screw, slide, or snap onto cannula hub 108 or otherwise attach to cannula hub 108.

Cannula hub 108 and cannula 110 may be removed from syringe system 100. This may generally be done after cannula 110 is used to draw medication into the interior of barrel 102. As illustrated in FIG. 4B, after cannula hub 108 and cannula 110 are removed from syringe system 100 cannula cover 112 might be used to cover plastic needle 114. For example, cannula cover 112 might screw, slide, snap, or pressure fit onto barrel 102, or otherwise attach onto barrel 102.

First end 118 may extend beyond the end of plastic needle 114 to provide some protection from inadvertent sticks, which may also be lessened due to the bluntness of plastic needle 114. Some protection against contamination might also be provided. In syringe system 100 cannula cover 112 may provide these protections by attaching cannula cover 112 to plastic needle 114 at cannula cover 112 first end 118 as illustrated in FIG. 4B. Accordingly, cannula cover 112 also acts as a cover for plastic needle 114, for example, when it is not covered by cannula hub 108. This may avoid a need for multiple covers.

FIG. 5 is a diagram illustrating a cannula 110 in accordance with an embodiment of the systems and methods described herein. Cannula 110 is a hollow tube 500 with an outside diameter "D" and an inside diameter "d." Medication or other fluids might flow inside hollow tube 500, for example, when installed on a cannula hub 108 that is attached to syringe system 100. In one embodiment, the cannula is formed of metal, such as stainless steel.

In some embodiments, one end of cannula 110 may be cut at an angle "α" to allow for cannula 110 to pierce a rubber stopper on top of a medication or drug vial, and to match an interior surface of the vial as discussed below. The total length of cannula 110 is indicated by "L" and the exposed length of cannula 110 is indicated by $L_1$. Because of angle "α" one side of cannula 110 will be shorter than the other. The cannula may have a wall thickness greater than a standard wall thickness for a given cannula gauge. Having a wall thickness greater than a standard wall thickness reduces the flexibility of the cannula shaft, while minimizing the dead space. In a specific embodiment D is 0.900±0.013 mm, d is 0.432±0.025 mm, L is 39.3±0.75 mm, $L_1$ is 33±1.5 mm, and "α" is 30±2°. As illustrated in FIG. 5, L indicates the total length of cannula 110, while $L_1$ is the exposed length of cannula 110. It will be understood that different lengths, angles, diameters, and tolerances are possible in other embodiments.

An angle selected for distal end of cannula 110 might be such that the likelihood of piercing a patient's skin is lessened somewhat relative to a typical metal medical needle. Additionally, the angle of the cannula 110 is selected so that when pressed through the top of a vial of medication it does not core. Further, the angle might be selected to match an angle at the bottom of a vial. Selecting such an angle may increase the amount of medication cannula 110 can withdraw from the vial. For example, in some embodiments, cannula assembly 128 may include a cannula 110 having a distal tip that is angled at an angle α to match at least a portion of an interior surface of a drug vial. Cannula 110 might then be positioned in alignment with the portion of the interior of the vial to remove substantially all of a material from the vial.

FIGS. 6A-6B are diagrams illustrating a plastic needle 114 and barrel 102 in accordance with an embodiment of the systems and methods described herein. In FIGS. 6A-6B cannula assembly 128 is not shown, however, the illustrated example includes threads 120 that may be used to attach cannula assembly 120 to an end of barrel 102. For example, second end 116 of cannula cover 112 may include a ridge that may be screwed into threads 120 to attach cannula cover 112 to barrel 102. As illustrated in FIGS. 6A-B threads 120 may be located between an outer wall of plastic needle 114 and a distal inner wall of barrel 102 forming threads 120. It will be understood that other attachment methods might be used in some embodiments.

Figure 7:
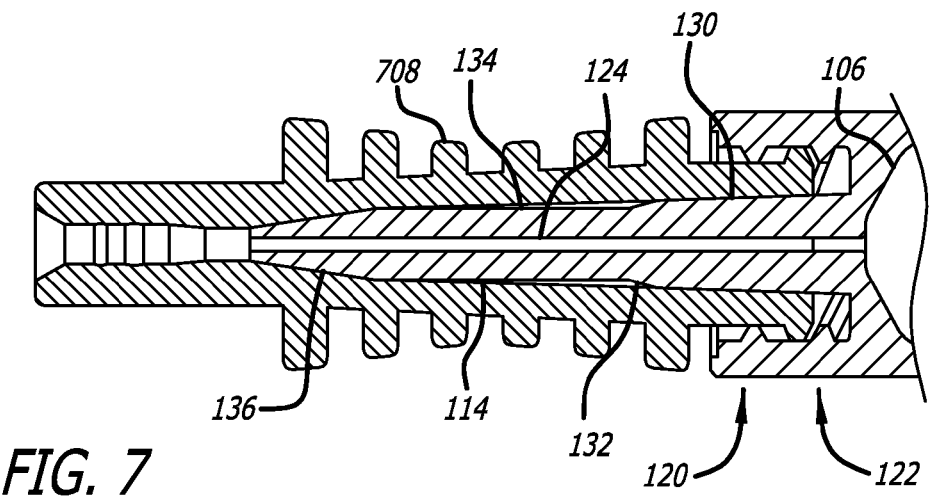
FIG. 7 is a diagram illustrating a plastic needle and a cannula hub without a cannula in accordance with an embodiment of the systems and methods described herein.

FIG. 7 is a diagram illustrating plastic needle 114 and another cannula hub 708. To provide a larger view of the cutaway of cannula hub 708 it is illustrated without cannula 110. Cannula hub 708 may be installed over plastic needle 114 and screwed into threads 120. In the illustrated embodiment, the threads are located inside an end portion of plastic needle 114. In another embodiment, threads may be part of an end of the barrel 102 such that the hub threads into barrel 102 directly, rather than the end of the plastic needle 114. Some embodiments might use other connection types to connect the cannula hub 708 to the needle barrel 102 or plastic needle 114. For example, cannula hub 708 may snap into end of the barrel 102 or the end of the plastic needle 114.

Some embodiments may include a proximal taper 130 which, in one embodiment has a ratio of 6% for example. In the illustrated embodiment a double taper 130, 136, including proximal taper 130 and distal taper 136 is illustrated. Moving distally along plastic needle 114 a generally parallel portion 134 is illustrated. It will be understood, however, that in other embodiments generally parallel portion 134 might be replaced by a tapered portion. Plastic needle 114 also includes a reduced diameter portion 132, as illustrated.

Double taper 130, 136 can seal against leakage of air or liquid. For example, each taper 130, 136 may contact a corresponding portion of cannula hub 708. These contacts between the tapers 130, 136 and the corresponding portion of cannula hub 708 may make it more difficult for air to leak into the device or liquid to leak from the device. Double taper 130, 136 is discussed further with respect to FIG. 8, which provides an isolated view of plastic needle 114.

Additionally, plastic needle 114 may have less dead space relative to needles in other syringe systems because it might be shorter than a typical cannula or needle used in such a typical system. Additionally, piston 106 may be shaped to fit snuggly against an end 122 of barrel 102 such that all or nearly all of the medication, liquid, or other substance is ejected from the interior of the barrel 102 into plastic needle 114. (Most of the material might also be ejected from plastic needle 114.) Additionally, the interior passage 124 of the plastic needle might be narrow to limit dead space.

Figure 8:
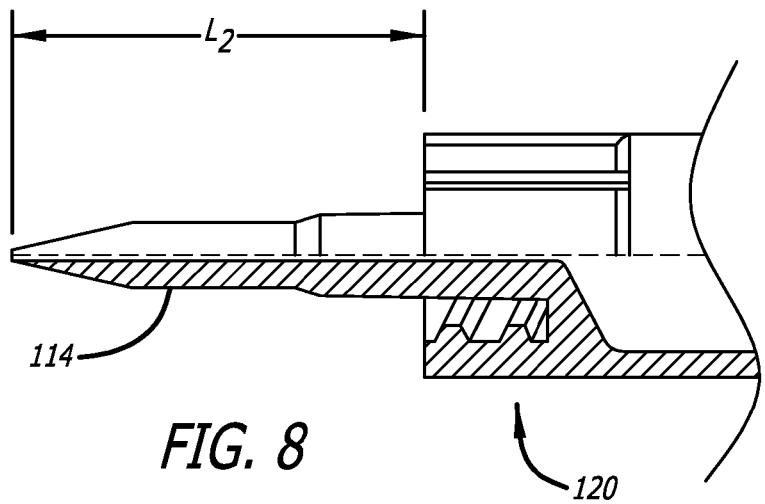
FIG. 8 is a diagram illustrating a plastic needle in accordance with an embodiment of the systems and methods described herein.
Figure 9:
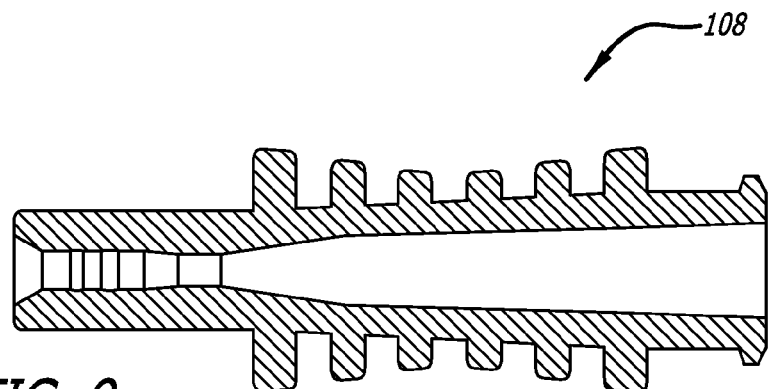
FIG. 9 is a diagram illustrating a cut away view of a cannula hub without a cannula in accordance with an embodiment of the systems and methods described herein.

FIGS. 8 and 9 provide isolated views of plastic needle 114 and cannula hub 708 respectively. As discussed above, FIG. 8 is a diagram illustrating an isolated view of plastic needle 114 in accordance with an embodiment of the systems and methods described herein. As illustrated, plastic needle 114 may have a double taper 103, 136. The over-all length of plastic needle 114 is indicated by $L_2$. Generally, $L_2$ will be long enough to go through the septum in an injection port. It will be understood that many different combinations of lengths, $L_2$ and $L_3$ might be used.

In the illustrated example, plastic needle 114 includes the proximal taper 130 at a proximal end of plastic needle 114. Proximal taper 130, tapers from a proximal first end to a proximal second end toward a longitudinal axis of plastic needle 114. Through this taper the diameter of plastic needle 114 changes from a first diameter of the needle 114 to a second diameter of the needle 114 that is less than the first diameter. Plastic needle 114 further includes a distal taper 136 at a distal tip of plastic needle 114. Distal taper 136 tapers from a distal first end to a distal second end toward the longitudinal axis from the second diameter to a third diameter of the needle less than the second diameter. Additionally, in the illustrated embodiment, the distal first end separated from the proximal second end.

Figure 10:
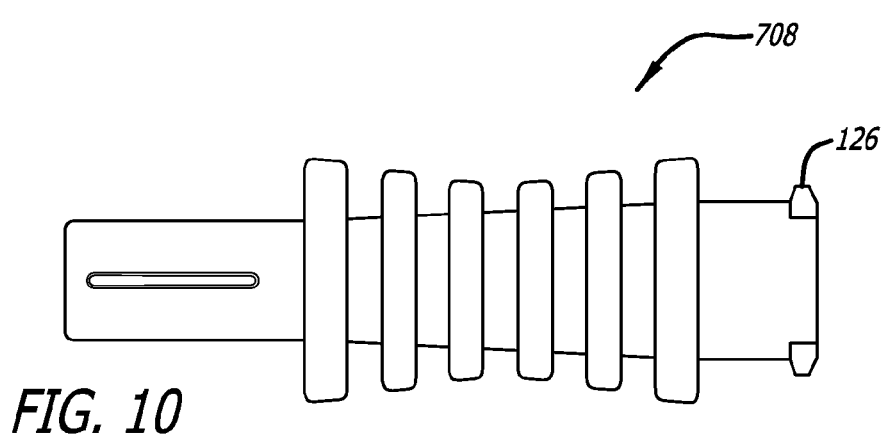
FIG. 10 is a diagram illustrating the cannula hub of FIG. 9.

FIG. 9 is a diagram illustrating an isolated cut away view of another cannula hub 708 in accordance with an embodiment of the systems and methods described herein. FIG. 10 is a diagram illustrating additional details of cannula hub 708 of FIG. 9. In some embodiments, cannula hub 708 may be coupled to an end of the barrel 102. For example, plastic needle 114 may screw into threads 120 located in barrel 102. Cannula hub 708 may include ridges 126 that screw into threads 120 to attach cannula hub 708 to barrel 102.

Figure 11:
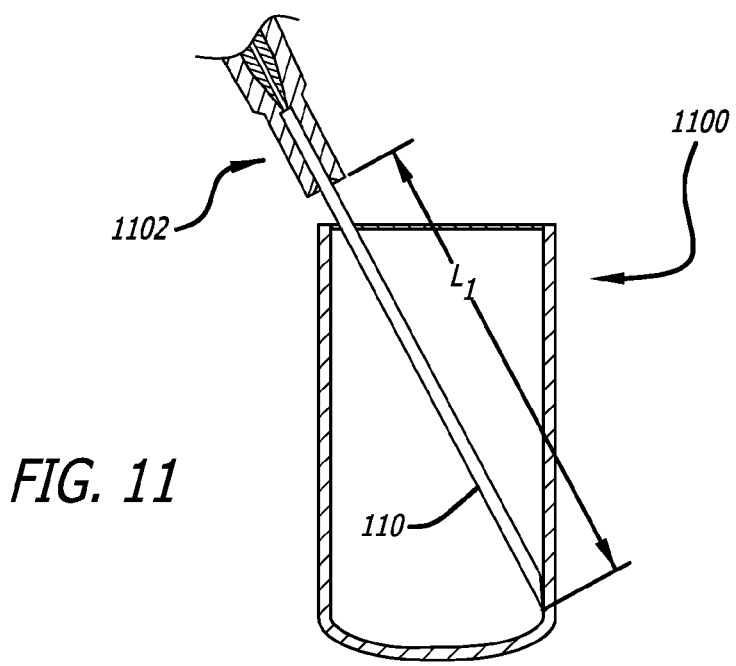
FIG. 11 is a diagram illustrating a vial and a cannula end in accordance with an embodiment of the systems and methods described herein.

FIG. 11 is a diagram illustrating a vial 1100 and a cannula 110 end in accordance with an embodiment of the systems and methods described herein. As illustrated in FIG. 11 the end of cannula 110 may be angled to match or approximately match a portion of vial 1100. Because vial 1100 may be curved, the angle might not match exactly. A small difference between the angle of cannula 110 and the portion of vial 1100 may, however, allow liquid to flow into cannula 110 more easily.

Matching or approximately matching an angle between cannula 110 and vial 1100 might generally increase the amount of a substance, such as a drug, that may be removed from vial 1100. Accordingly, less of the substance might be left in vial 1100 after a final dose is removed from vial 1100. It will be understood that, after a final dose is removed from vial 1100, all of the substance might be removed or some amount of the substance might still be in vial 1100.

It will be understood that a cannula 110, according to embodiments described herein, may have different angles and lengths so that a particular cannula angle and length combination might be used for various vials having corresponding dimensions, as described below. In other words, each vial design might be used in conjunction with a cannula 110 specifically designed for use with that vial design. In addition to the end angle of a cannula 110 that may generally match the bottom of a vial. In some examples, however, the bottom of vial 1100 may be rounded. Accordingly, the angle might match a specific portion of the bottom of vial 1100. Additionally, it will be understood that some differences in the vial angle and the cannula 110 may allow the material in the vial to have better access to the cannula 110. For example, if cannula 110 and vial 1100 bottom match there may be little or no space left for the material in vial 1100 to flow into cannula 110.

Additionally, the exposed length, $L_1$, of the cannula 110 may be selected to provide some minimal clearance beyond the top of the vial 1100, as indicated by 1102. This can decrease the amount of materials used because some materials can be left behind in cannula 110. Additionally, it may decrease stresses on cannula 110 because smaller lengths will impart a smaller bending moment on cannula 110 for a given force.

It will also be understood that cannula 110 may be designed to enter a vial 1100 at a specific angle. Accordingly, the angle of an end of a cannula 110 may be designed to be angled to match or approximately match a portion of vial 1100 when the cannula enters the vial at approximately that specific angle. Additionally, the length of cannula 110 can be selected to provide some minimal clearance beyond the top of the vial 1100 when cannula 110 enters vial 1100 at approximately that specific angle. The minimal clearance might be such that the end of the plastic needle 114 is just above the top of vial 1100 when cannula 110 is inserted into the vial 1100, as indicated at 1102. Alternatively, additional clearance might be provided, e.g., 0 to 5 mm or more.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A syringe system, including a barrel, plunger and piston, comprising:
   a plastic needle coupled to an end of the barrel, the needle including a proximal taper at a proximal end of the needle, tapering from a proximal first end to a proximal second end toward a longitudinal axis of the needle from a first diameter of the needle to a second diameter of the needle less than the first diameter, the needle further including a distal taper at a distal tip of the needle, tapering from a distal first end to a distal second end toward the longitudinal axis from the second diameter to a third diameter of the needle less than the second diameter, the distal first end separated from the proximal second end; and
   a cannula assembly including a cannula and cannula hub, the cannula hub having an internal first mating surface that contacts the proximal taper of the needle and an internal second mating surface that contacts the distal taper of the needle, the cannula assembly removably coupled to the plastic needle.

2. The syringe system according to claim 1, wherein the proximal and distal taper interact with the cannula hub to provide a liquid seal and an air seal.

3. The syringe system according to claim 1, wherein the cannula includes a non-coring distal tip that is angled to match a portion of an interior surface of a drug vial.

4. The syringe system according to claim 3, wherein the cannula has a length that permits the distal tip to reach an interior bottom side surface of a vial when inserted therein.

5. The syringe system according to claim 1, wherein a first end of the cannula hub screws into a portion of the plastic needle at a first end of the barrel.

6. The syringe system according to claim 1, wherein the plastic needle has a length less than a length of the cannula.

7. The syringe system according to claim 1, wherein the piston is shaped to contact an interior surface of the plastic needle to eliminate dead space therebetween.

8. The syringe system according to claim 1, further comprising a cannula cover having a first end, including a first internal surface mating with an exterior surface of the cannula assembly for removable attachment thereto, and a second end opposite the first end, including a second internal surface mating with an exterior surface of the barrel for removable attachment thereto.

9. A syringe system, including a barrel, plunger and piston, comprising:
   a plastic needle coupled to an end of the barrel, the needle including a proximal taper at a proximal end of the needle, tapering from a proximal first end to a proximal second end toward a longitudinal axis of the needle from a first diameter of the needle to a second diameter of the needle less than the first diameter, the needle further including a distal taper at a distal tip of the needle, tapering from a distal first end to a distal second end toward the longitudinal axis from the second diameter to a third diameter of the needle less than the second diameter;
   a cannula assembly removably coupled to the plastic needle; and
   a cannula cover having a first end, including a first internal surface mating with an exterior surface of the cannula assembly for removable attachment thereto, and a second end opposite the first end, including a second internal surface mating with an exterior surface of the barrel for removable attachment thereto.

10. The syringe system according to claim 9, wherein the first end of the cannula cover friction fits onto the hub.

11. The syringe system according to claim 9, wherein the second end of the cannula cover screws into an end of the barrel.

12. The syringe system according to claim 9, wherein the proximal and distal taper interact with the cannula hub to provide a liquid seal and an air seal.

13. The syringe system according to claim 9, wherein the cannula includes a non-coring distal tip that is angled to match a portion of an interior surface of a drug vial.

14. The syringe system according to claim 9, wherein the distal first end of the plastic needle is separated from the proximal second end of the plastic needle by a length.

15. The syringe system according to claim 9, wherein the cannula assembly includes a cannula and cannula hub, the cannula hub having an internal first mating surface that contacts the proximal taper of the needle and an internal second mating surface that contacts the distal taper of the needle.

16. A syringe system, including a barrel, plunger and piston, comprising:
   a plastic needle coupled to an end of the barrel, the needle including a proximal taper at a proximal end of the needle, tapering from a proximal first end to a proximal second end toward a longitudinal axis of the needle from a first diameter of the needle to a second diameter of the needle less than the first diameter, the needle further including a distal taper at a distal tip of the needle, tapering from a distal first end to a distal second end toward the longitudinal axis from the second diameter to a third diameter of the needle less than the second diameter, the distal first end separated from the proximal second end; and
   a cannula assembly removably coupled to the plastic needle, including:
      a cannula having a distal tip cut at an angle a to match a portion of an interior surface of a drug vial, wherein the cannula is positioned in alignment with the portion of the interior surface of the vial to remove substantially all of a material from the drug vial; and
      a cannula hub having an internal first mating surface that contacts the proximal taper of the needle and an internal second mating surface that contacts the distal taper of the needle.

17. The syringe system according to claim 16, wherein the cannula has a length that permits the distal tip to reach an interior bottom side surface of a vial when inserted therein.

18. The syringe system according to claim 16, further comprising a cannula cover having a first end, including a first internal surface mating with an exterior surface of the cannula assembly for removable attachment thereto, and a second end opposite the first end, including a second internal surface mating with an exterior surface of the barrel for removable attachment thereto.

* * * * *

UNITED STATES PATENT AND TRADEMARK OFFICE
CERTIFICATE OF CORRECTION

| | | |
|---|---|---|
| PATENT NO. | : 8,333,737 B2 | Page 1 of 1 |
| APPLICATION NO. | : 12/793380 | |
| DATED | : December 18, 2012 | |
| INVENTOR(S) | : Shinya Nagase et al. | |

It is certified that error appears in the above-identified patent and that said Letters Patent is hereby corrected as shown below:

In the Claims

Column 10, claim 10, line 8, delete "hub" and insert --cannula assembly--.

Column 10, claim 12, line 13, delete "hub" and insert --assembly--.

Signed and Sealed this
First Day of July, 2014

Michelle K. Lee
*Deputy Director of the United States Patent and Trademark Office*